US00PP33553P2

(12) United States Plant Patent
Van Swieten

(10) Patent No.: US PP33,553 P2
(45) Date of Patent: Oct. 12, 2021

(54) ***PHALAENOPSIS* ORCHID PLANT NAMED 'PHALJALZE'**

(50) Latin Name: ***Phalaenopsis* hybrid**
Varietal Denomination: PHALJALZE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,234

(22) Filed: Apr. 21, 2021

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

Pluto Plant Variety Database Jul. 10, 2021. p. 1.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHALJALZE', particularly characterized by copper, striped flowers with reddish-purple lips, flowers with a convex shape in lateral view, lateral sepals with a recurving curvature of the longitudinal axis, and is propagated by meristem tissue culture, is disclosed.

3 Drawing Sheets

Genus and species: *Phalaenopsis* hybrid.
Variety denomination: 'PHALJALZE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALJALZE'.

The new *Phalaenopsis* plant is a product of a planned breeding program conducted by the inventor in Bleiswijk, the Netherlands. The objective of this breeding program was to create a new *Phalaenopsis* plant with copper, striped flowers with reddish-purple lips, suitable for potted plant production.

The new *Phalaenopsis* plant 'PHALJALZE' is a result of cross-pollination made by the inventor in June 2013 in Bleiswijk, the Netherlands, of the proprietary female, or seed parent, *Phalaenopsis* hybrid '24531-01' (unpatented) with the proprietary male, or pollen parent, *Phalaenopsis* hybrid 'PHALIFQUDI' (U.S. Plant Pat. No. 26,831).

The new *Phalaenopsis* was selected by the inventor as a single plant within the progeny of the stated cross-pollination in a controlled greenhouse in Bleiswijk, the Netherlands, in May 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 9, 2020 (Application no. 2020/1007), by Applicant who obtained the subject matter disclosed directly from the inventor. 'PHALJALZE' has not been made publicly available or sold anywhere in the world prior to the effective filing date of this application with the exception of sales or disclosures made one year or less before the effective filing date of this claimed invention by Applicant who obtained 'PHALJALZE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALJALZE' as a new and distinct variety of *Phalaenopsis* plant:

1) Copper, striped flowers with reddish-purple lips;
2) Flower shape in lateral view is convex; and
3) Curvature of longitudinal axis of lateral sepals is recurving.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in March 2021. Colors in the photographs may differ from the color values cited in the detailed botanical description, which accurately describe the actual colors of the new variety.

DESCRIPTION OF THE NEW VARIETY

Figure 1:
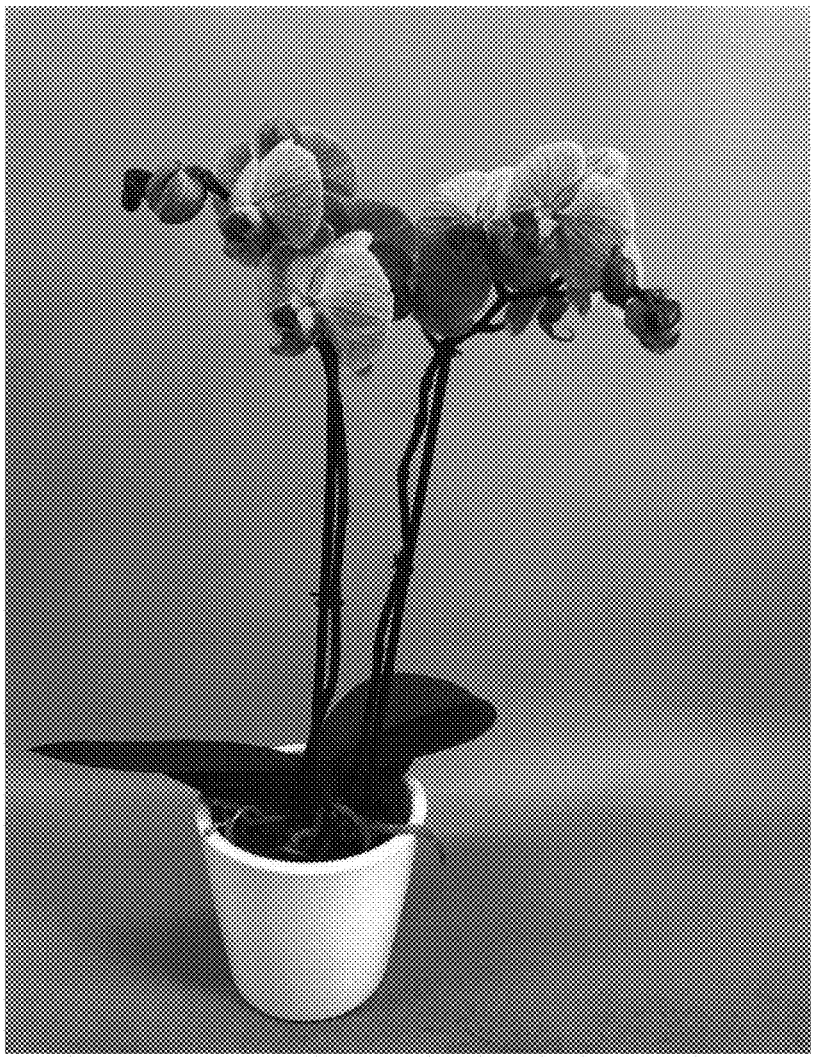
FIG. 1 shows the overall plant habit, including blooms, buds, and foliage of 'PHALJALZE'.
Figure 2:
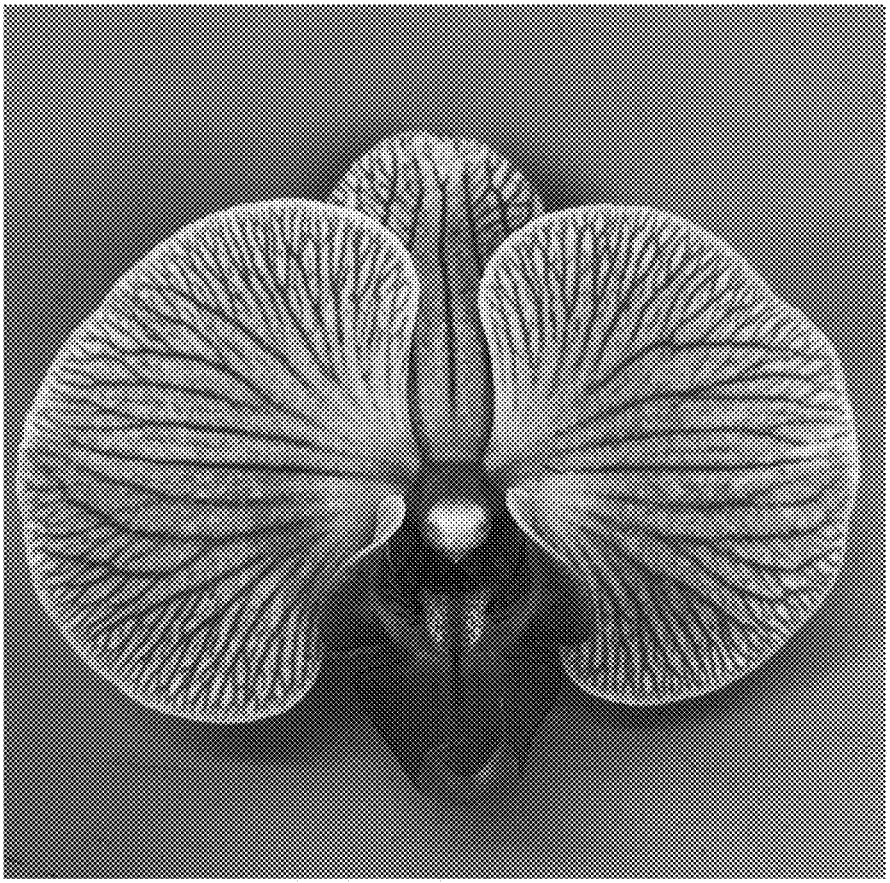
FIG. 2 shows a close-up of a flower of 'PHALJALZE'.
Figure 3:
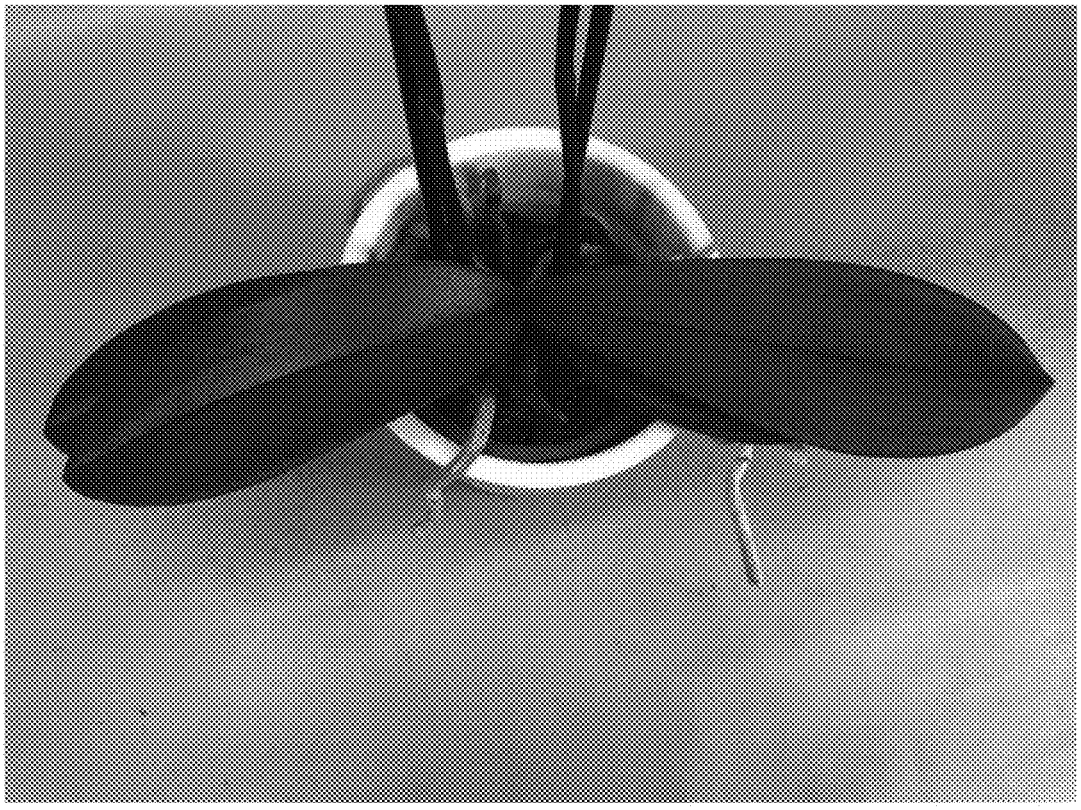
FIG. 3 shows an overhead view of the leaves of 'PHALJALZE'.

The following detailed description sets forth the distinctive characteristics of 'PHALJALZE'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALJALZE'.

Parentage:

*Female parent*.—*Phalaenopsis* cultivar '24531-01' (unpatented).

*Male parent*.—*Phalaenopsis* cultivar 'PHALIFQUDI' (U.S. Plant Pat. No. 26,831).

Propagation:

*Type*.—Meristem tissue culture.

Roots:

*Root description*.—Greyed-green (a color in between RHS 190B and RHS 190C) colored roots with a touch of dark pink (RHS 182C) with branching lateral roots having very small yellowish-green (RHS N144A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 50.0 cm to 55.0 cm.

*Width* (*measured from leaf tips*).—About 33.0 cm to 35.0 cm.

*Vigor*.—Strong.

Leaves:

*Mature leaves*.—Quantity per plant: 8 to 9 leaves are produced before flowering. Length (fully expanded): 16.0 cm to 21.0 cm. Width: 6.5 cm to 7.5 cm. Position of the broadest part of the leaf: Toward the tip. Shape: Obovate. Base shape: Moderately elongated. Apex: Almost equal obtuse. Leaf blade angle with the petiole (measured from the horizontal position): Between 10 degrees and 30 degrees. Leaf margin: Entire. Color: Upper surface: Yellow-green (RHS 146A) with a dark red-purple margin (a color in between RHS 187A and RHS N77A) toward the tip. Lower surface: Dark red-purple (a color in between RHS 187A and RHS N77A) with a touch of yellow-green (RHS 146B). Texture (both upper and lower surfaces): Smooth. Thickness: 2.0 mm to 3.0 mm. Variegation: Absent. Venation: Pattern: Parallel. Color of the midvein: Upper surface: Dark red-purple (a color in between RHS 187A and RHS N77A). Lower surface: Purple (RHS N77A).

Peduncle:

*Quantity per plant*.—1 to 2.

*Number of flowers per peduncle*.—8 to 12.

*Length*.—50.0 cm to 55.0 cm.

*Diameter*.—4.0 mm to 5.0 mm.

*Strength*.—Strong.

*Aspect*.—Upright to slightly pendent.

*Texture*.—Smooth.

*Color*.—Dark red-purple (a color in between RHS 187A and RHS N77A).

*Internode length*.—3.0 cm to 4.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 180.0 mm to 230.0 mm.

*Flowering time*.—First flowers can be expected 10 to 11 months after planting in a 12-cm pot.

*Flower*.—Height: 80.0 mm to 85.0 mm. Diameter: 85.0 mm to 90.0 mm. Depth of lip: 21.0 mm to 23.0 mm.

*Flower longevity*.—On the plant: 12 to 14 weeks.

*Flower shape*.—Convex.

*Fragrance*.—Absent.

*Flower bud*.—Average size: Medium to large. Length: 21.0 min to 23.0 mm. Width: 18.0 mm to 20.0 mm. Shape: Egg shaped. Color: Light yellow-green (RHS 160C) with greyish-red (RHS 182B) and purplish-red shade and stripes (RHS N77B).

*Petals*.—Arrangement: Open/free. Shape: Semi-circular. Apex: Rounded asymmetric. Margin: Moderately undulated. Length (from base to tip): 39.0 mm to 41.0 mm. Width: 53.0 mm to 55.0 mm. Position of the broadest part of the petal: Toward the base. Color (when fully opened): Upper surface: Basic color: Light greenish-yellow (RHS 4C). Over color: Touch of light greenish-yellow (RHS 4C) at the base; dark pink shade (RHS 182C); purplish-red stripes (a color in between RHS 185B and RHS 185C). Lower surface: Basic color: Light greenish-yellow (RHS 160C). Over color: Touch of light yellow (RHS 160B) at the base; dark pink (RHS 182C) and purplish-pink stripes (a color in between RHS 185C and RHS 185D). Number of spots and stripes on the petals (upper surface): Many stripes. Color of spots and stripes on the petals (upper surface): A color in between RHS 185C and RHS 185D. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 40.0 mm to 42.0 mm. Width: 29.0 mm to 31.0 mm. Position of the broadest part of the dorsal sepals: At the middle. Color (when fully opened): Upper surface: Basic color: Light yellow (RHS 160B). Over color: Dark pink (RHS 182D) at the base; purplish-red stripes and netting (RHS 186A). Lower surface: Basic color: Light greenish-yellow (RHS 160C). Over color: Dark pink shade (RHS 182C); purplish-red stripes and netting (RHS 186B). Number of spots and stripes on the dorsal sepals (upper surface): Medium stripes. Color of spots and stripes on the dorsal sepals (upper surface): RHS 186A. Density of netting of the dorsal sepals (upper surface): Medium. Color of the netting: RHS 186A.

*Lateral sepals*.—Shape: Ovate. Apex: Obtuse symmetric. Margin: Entire. Length (from base to tip): 40.0 mm to 42.0 mm. Width: 26.0 mm to 28.0 mm. Position of the broadest part of the lateral sepals: At the base. Color (when fully opened): Upper surface: Basic color: Light yellow (RHS 160B). Over color: Greyed-red shade (RHS 182B); reddish-purple stripes and netting (a color in between RHS 185B and RHS 185C). Lower surface: Basic color: Light greenish-yellow (RHS 160C). Over color: Dark pink shade (RHS 182C); diluting purplish-red stripes (RHS 186A). Number of spots and stripes on the lateral sepals (upper surface): Medium stripes. Color of spots and stripes on the lateral sepals (upper surface): A color in between RHS 185B and RHS 185C. Density of netting of the lateral sepals (upper surface): Medium. Color of the netting (upper surface): A color in between RHS 185B and RHS 185C.

*Labellum* (*lip*).—Whiskers: Present. Length of whiskers: 9.0 mm to 11.0 mm. Color of whiskers: Purplish-pink (RHS N78C) at the base; red (RHS 184B) with white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 17.0 mm to 19.0 mm. Width: 13.0 mm to 15.0 mm. Color: Upper surface: Touch of greenish-yellow (RHS 6C) and striped (RHS 187C) at the base; reddish-orange region (RHS 174C) at the middle; dark reddish-orange (RHS 175B) toward margin on one side; white margin (RHS NN155C) on the other side; reddish-purple stripes (RHS N78B) toward the tip. Lower surface: Dark pink (RHS 182C) at the base; dark reddish-orange (RHS 175C) toward margin on one side; yellowish-white margin (RHS 158D) on the other side; purplish-pink (RHS N78C) toward the tip. Number of spots and stripes on the lateral lobe: Many stripes. Color of spots and stripes on the lateral lobe: At the base RHS 187C and toward the tip RHS N78B. Density of netting of the lateral lobe: None. Color of the netting: Not applicable.

*Apical lobe*.—Shape: Triangular. Margin: Entire. Length: 20.0 mm to 22.0 mm. Width: 18.0 mm to 20.0 mm. Color: Upper surface: Greenish-yellow (RHS 6B) and dark reddish-orange margin (RHS 175B) at the base and toward wings; reddish-purple (a color in between RHS NN74B and RHS N78B) toward whiskers. Lower surface: Dark reddish-orange margin (RHS 175B); yellowish-white (RHS N155D) at the middle from base toward whiskers and light yellow (RHS 161C) toward wings; purplish-pink (RHS N78C) toward margins on both sides; white region (RHS NN155C) at the middle toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Medium to large. Height: 7.0 mm to 8.0 mm. Length: 6.0 mm to 7.0 mm. Width: 4.0 mm to 5.0 mm. Color: Light greenish-yellow (RHS 4C) with greenish-yellow tips (RHS 6A); dark pink (RHS 182D) on sides; red (RHS 180C) on the backside; dotted (RHS 59B).

Reproductive organs:

*Column*.—Length: 8.0 mm to 10.0 mm. Diameter: 5.0 mm to 6.0 mm. Color: Reddish-purple (RHS N78B).

*Pollinia*.—Quantity: 2. Diameter: 0.8 mm to 1.0 mm. Color: Orange (RHS 24A).

*Ovary*.—Length: 14.0 mm to 16.0 mm. Diameter: 2.5 mm to 2.7 mm.

*Pedicel*.—Length: 42.0 mm to 44.0 mm. Diameter: 2.9 mm to 3.3 mm. Color: Touch of dark purplish-red (RHS N79B) at the base; yellow-green (RHS 145C); light reddish-purple (RHS N78D). Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALJALZE' differs from the female parent plant '24531-01' (unpatented) in that 'PHALJALZE' has apical lobes with a main color of reddish-purple and whiskers that are purplish-pink at the base and red with white tips, whereas '24531-01' has apical lobes with a main color of white and whiskers that are white with yellow tips.

'PHALJALZE' differs from the male parent plant 'PHALIFQUDI' (U.S. Plant Pat. No. 26,831) in that 'PHALJALZE' has whiskers that are purplish-pink at the base and red with white tips, whereas 'PHALIFQUDI' has whiskers that are purplish-red with small yellow tips. Additionally, 'PHALJALZE' has larger flowers than 'PHALIFQUDI'.

'PHALJALZE' is most similar to the commercial *Phalaenopsis* plants named 'PHALCITADE' (unpatented) and 'PHALKUZEL' (U.S. Plant Pat. No. 30,723). 'PHALJALZE' differs from the commercial variety 'PHALCITADE' in that 'PHALJALZE' has apical lobes with a main color of reddish-purple and reddish-purple columns, whereas 'PHALCITADE' has apical lobes with a main color of light purple and light purple columns.

'PHALJALZE' differs from the commercial variety 'PHALKUZEL' in that 'PHALJALZE' has triangular apical lobes, spatulate lateral lobes, reddish-purple columns and medium to large calluses, whereas 'PHALKUZEL' has rhombic apical lobes, weakly spatulate lateral lobes, light purple columns, and small calluses.

I claim:

1. A new and distinct variety of *Phalaenopsis* plant named 'PHALJALZE', substantially as described and illustrated herein.

* * * * *